(12) United States Patent
Park et al.

(10) Patent No.: US 7,790,424 B2
(45) Date of Patent: Sep. 7, 2010

(54) L-METHIONINE PRODUCING MICROORGANISM AND METHOD OF PRODUCING L-METHIONINE USING THE MICROORGANISM

(75) Inventors: Young Hoon Park, Seongnam-si (KR); Kwang Myung Cho, Goyang-si (KR); Yong-Uk Shin, Yongin-si (KR); Hyewon Um, Suwon-si (KR)

(73) Assignee: CJ Cheiljedang Corporation, Seoul (KR)

( * ) Notice: Subject to any disclaimer, the term of this patent is extended or adjusted under 35 U.S.C. 154(b) by 397 days.

(21) Appl. No.: 11/631,024

(22) PCT Filed: Jun. 16, 2005

(86) PCT No.: PCT/KR2005/001849

§ 371 (c)(1),
(2), (4) Date: Oct. 3, 2007

(87) PCT Pub. No.: WO2006/001616

PCT Pub. Date: Jan. 5, 2006

(65) Prior Publication Data

US 2008/0194030 A1   Aug. 14, 2008

(30) Foreign Application Priority Data

Jun. 29, 2004   (KR) .................. 10-2004-0049740

(51) Int. Cl.
*C12P 13/12* (2006.01)
*C12N 1/21* (2006.01)
(52) U.S. Cl. ................ 435/113; 435/252.3; 435/252.33
(58) Field of Classification Search .................. None
See application file for complete search history.

(56) References Cited

U.S. PATENT DOCUMENTS

| 6,355,454 | B1 | 3/2002 | Marx et al. | |
|---|---|---|---|---|
| 7,510,854 | B2* | 3/2009 | Pompejus et al. | 435/69.1 |
| 2002/0049305 | A1* | 4/2002 | Bathe et al. | 530/350 |
| 2003/0092026 | A1 | 5/2003 | Rey et al. | |
| 2007/0026505 | A1* | 2/2007 | Madden et al. | 435/106 |
| 2007/0122888 | A1* | 5/2007 | Boy et al. | 435/113 |
| 2008/0118959 | A1* | 5/2008 | Schroder et al. | 435/113 |
| 2008/0318790 | A1* | 12/2008 | Ebneth et al. | 504/307 |

FOREIGN PATENT DOCUMENTS

| EP | 1239041 A2 | 9/2002 |
|---|---|---|
| JP | 2000-139471 | 5/2000 |
| KR | 1992-0012423 A | 7/1992 |
| KR | 1019920008365 B1 | 9/1992 |
| WO | WO 02/10206 A | 2/2002 |
| WO | WO 02/10208 A | 2/2002 |

OTHER PUBLICATIONS

Mischoulon D. et al, "Role of S-adenosyl-L-methionine in the treatment of depression: a review of the evidence," Am J. Clin Nutr, Nov. 2002; 76(5): 1158S-61S.

Mato JM., "S-Adenosylmethionine: a control switch that regulates liver function," Jan. 2002; FASEB J. 16(1): 15-26.

Sander O. "Review: S-adenosylmethionine treats osteoarthritis as effectively as nonsteroidal anti-inflammatory drugs with fewer adverse effects," ACP J Club, Jan.-Feb. 2003; 138(1): 21.

Soeken KL et al, "Safety and efficacy of S-adenosylmethionine (SAMe) for osteoarthritis," J Fam Pract., May 2002; 51(5): 425-30.

Lockwood DS et al, D-Methionine Attenuates Inner Hair Cell Loss in Carboplatin-treated Chinchillas, Audiol Neurootol., Sep.-Oct. 2000; 5(5): 263-266.

Biran, Dvora et al, Control of Methionine biosynthesis in *Escherichia coli* by proteolysis: Molecular Microbiology (2000) 37(6), 1436-1443.

Wahl, Markus C. et al, "Cloning, purification, crystalization, and preliminary x-ray diffraction on analysis of crystathionine Y-synthase from *E. coli*," FEBS Letters, vol. 414, Issue 3, Sep. 15, 1997, pp. 492-496.

Kanzaki, Hiroshi et al, "Distribution of two kinds of cystathionine Y-synthase in various bacteria," FEMS Microbiology Letters, vol. 33(1) Jan. 1986, pp. 65-68.

Lawther RP et al, "The complete nucleotide sequence of the ilvGMEDA Operon of *Escherichia coli* K-12," Nucleic Acids Res 1987; 15(5); 2137-55.

Clausen T et al, "Crystal structure of *Escherichia coli* crystathionine Y-synthase at 1.5 A resolution," EMBO J. Dec. 1, 1998; 17(23): 6827-38.

Martel A et al, "Pyridoxal 5' phosphate binding site of *Escherichia coli* Beta cystathionase and cystathionine gamma synthase comparison of their sequences," Biochem Biophys Tes Commun 1987; 147 (2); 565-71.

Dwivedi CM, "Cloning, purification and characterization of B-cystathionase from *Escherichia coli*," Biochemistry 1982; 21(13); 3064-9.

Sheppard CA et al, "Purification and Properties of NADH-Dependent 5,10-Methylenetetrahydrofolate Reductase (MetF) from *Escherichia coli*," J Bacteriol 1999; 181(3); 718-25.

Shstak K et al, "Serine Hydroxymethyltransferase: Mechanism of the Racemization and transamination of D- and L-Alanine," Biochemistry 1988; 27(21); 8007-14.

Saint-Girons I et al, "Nucleotide sequence of metF, the *E. coli* structural gene for 5-10 methylene tetrahydrofolate reductase and of its control region," Nucleic Acids Res 1983; 11(19); 6723-32.

(Continued)

*Primary Examiner*—Nancy Vogel
(74) *Attorney, Agent, or Firm*—Casimir Jones, S.C.

(57) ABSTRACT

Disclosed herein are a method of preparing an L-methionine production strain by overexpressing proteins involved in L-methionine biosynthesis in an L-threonine production strain, a strain prepared by the method, and a method of producing L-methionine using the strain.

15 Claims, 5 Drawing Sheets

OTHER PUBLICATIONS

Plamann MD et al, "Complete nucleotide sequence of the *E. coli* glyA gene," Nucleic Acids Res 1983; 11(7); 2065-75.

Blattner et al, "The Complete Genome Sequence of *Escherichia coli* K-12," Science (1997) 277; 1453-1462.

English Translation of Abstract; Korean Publication No. KR 10199200008365(B1), Applicant: Cheil Sugar Co., Published Sep. 26, 1992 (Abstract Only) (1 PG.).

Jeon BR et al, "S-adenosylmethionine protects post-ischemic mitochondrial injury in rat liver," J Hepatol, Mar. 2001; 34(3) 395-401.

Datta P et al, "Covalent structure of biodegradative threonine dehydratase of *Escherichia coli*: Homology with other dehydratases," Patil RV 1987 Proc Natl Acad Sci USA 1987; 84(2) 393-7.

Shostak K et al, "Serine Hydroxymethyltransferase: Mechanism of the Racemization and Transamination of D- and L-Alanine," Biochemistry, (1988) 27(21); 8007-14.

Lee, James Prentice-Hall International Editions, Biochemical Engineering Manual of Methods for General Bacteriology by the American Society for Bacteriology, Washington D.C. US 1981, pp. 138-176.

Derwent, "Fermentative process for preparation of L-methionine, comprises using a modified Met producing microorganism particularly an *Escherichia* species," May 23, 2000.

* cited by examiner

Fig.1

5-MTHG: 5-methyltetrahydropteroyltri-L-glutamate
THG: Tetrahydropteroyltri-L-glutamate

L-METHIONINE PRODUCING MICROORGANISM AND METHOD OF PRODUCING L-METHIONINE USING THE MICROORGANISM

The present application is a national stage entry under 35 U.S.C. 371 of International Application Number PCT/KR2005/001849, filed Jun. 16, 2005, which claims priority to Korean application 10-2004-0049740, filed Jun. 29, 2004, each of which is herein incorporated by reference in its entirety.

TECHNICAL FIELD

The present invention relates to the production of L-methionine. More particularly, the present invention relates to a method of preparing an L-methionine production strain by overexpressing proteins involved in L-methionine biosynthesis in an L-threonine production strain, a strain prepared by the method, and a method of producing L-methionine using the strain.

BACKGROUND ART

Methionine, an essential amino acid for life, is used in many fields, including as a food additive, a feed, a material for various medicinal solutions and medicines, etc. Methionine acts as a precursor for choline (lecithin) and creatine and is used as a material for the systhesis of cysteine and taurine. Further, methionine plays a role in sulfur supply. S-adenosylmethionine (SAM), derived from L-methionine, serves as a methyl donor in vivo and is involved in the synthesis of various neurotransmitters in the brain. Methionine and/or S-adenosyl-L-methionine (SAM) is/are also found to prevent lipid accumulation in the liver and arteries and to be effective for the treatment of depression, inflammation, liver diseases and muscle pain.

As summarized below, methionine and/or S-adenosyl-L-methionine has been found, thus far, to have in vivo functions of:

1) helping prevent lipid accumulation in the liver, where lipid metabolism is mediated, and in arteries and maintaining blood flow to the brain, the heart and the kidneys (J Hepatol. Jeon B R et al., March 2001; 34(3): 395-401).

2) aiding digestion, detoxifying and excreting harmful agents, and scavenging heavy metals such as lead.

3) acting as an excellent antidepressant when methionine is administered in a dose of 800-1,600 mg of methionine per day (Am J Clin Nutr. Mischoulon D. et al., November 2002; 76(5): 1158S-61S).

4) improving liver functions against liver diseases (FASEB J. Mato J M., January 2002; 16(1): 15-26). Particularly, attenuating alcohol-induced liver injury (Cochrane Database Syst Rev., Rambaldi A., 2001; (4): CD002235).

5) showing an anti-inflammation effect on osteoarthritis and promoting the healing of joints (ACP J Club. Sander O., January-February 2003; 138(1): 21, J Fam Pract., Soeken K L et al., May 2002; 51(5): 425-30).

6) acting as an essential nutrition to hair to prevent brittle hair and depilation (Audiol Neurootol., Lockwood D S et al., September-October 2000; 5(5): 263-266).

Methionine, useful in the food industry and the medicine industry, can be produced in a chemical route or a biological route.

On the whole, chemical synthesis for the production of L-methionine utilizes the hydrolysis of 5-(β-methylmercaptoethyl)-hydantoin. However, the chemical systhesis suffers from the problem of synthesizing methionine in a mixture of L- and D-forms.

In the biological route, advantage is taken of the proteins involved in methionine production. Biosynthesis of L-methionine is achieved by converting homoserine into methionine with the aid of enzymes encoded by metA, metB, metC, metE, and metH genes. In detail, homoserine acetyltransferase which is the first enzyme in a methionine biosynthesis pathway and encoded by metA functions to convert homoserine into O-succinyl-L-homoserine. Subsequently, O-succinyl-L-homoserine is converted into cystathionine by O-succinylhomoserine lyase which is encoded by metB. Cystathionine beta lyase which is encoded by metC is responsible for the conversion of cystathionine into L-homocystein. Two enzymes, cobalamin-independent methionine synthase and cobalamin-dependent methionine synthase, which are respectively encoded by metE and metH, can catalyze the conversion of L-homocysteine into L-methionine. At this time, the metF gene product, 5,10-methylenetetrahydrofolate reductase and the glyA gene product, serine hydroxymethytransferase, synthesize, in cooperation, N(5)-methyltetrahydrofolate that acts as the donor of a methyl group necessary for the synthesis of L-methionine.

In the biological route, L-methionine is synthesized through a series of organic reactions by the enzymes. Thus, these enzymes and proteins controlling them may be used in the genetic manipulation for improving and controlling L-methionine synthesis. For example, Japanese Pat. Laid-Open Publication No. 2000-139471 discloses an L-methionine production method using *Escherichia* sp. in which metBL is overexpressed in the presence of a leaky type of metK, with thrBc and metJ eliminated. US 2003/0092026 A1 describes a *Corynerbacterium* sp. that is modified to remove metD, a factor inhibitory to L-methionine synthesis, therefrom. US 2002/0049305 discloses that the production of L-methionine can be improved by increasing the expression of 5,10-methylenetetrahydrofolate reductase (metF).

These biological processes, even though having the advantage of producing only L-methionine, have low production capacity. Extensive attempts for the improvement in fermentological processes, nutritive medium compositions and chromatographic processes have been made to increase the productivity of L-amino acids including L-methionine, but are proven to be insufficient.

Furthermore, when methionine is synthesized in a certain level or higher, it, as the final product, inhibits through feedback the gene transcription of the starting protein metA, which initiates the biosynthesis of methionine. In vivo, the level of methionine is regulated in such a manner that the transcription of the metA gene is inhibited by methionine and the metA product is broken down by protease in a translation stage. Accordingly, methionine cannot be increased to a certain level in vivo solely by the overexpression of the metA gene (Dvora Biran, Eyal Gur, Leora Gollan and Eliora Z. Ron: Control of methionine biosynthesis in *Escherichia coli* by proteolysis: Molecular Microbiology (2000) 37(6), 1436-1443).

Leading to the present invention, intensive and thorough research on L-methionine production, conducted by the present inventors, aiming at overcomining the problems encountered in prior arts, resulted in the finding that on the basis of the fact that the metB gene product O-succinylhomoserine lyase is able to synthesize O-succinyl-L-homoserine, an intermediate of the methionine biosynthesis, from the threonine hydrolysate 2-oxobutanoate, in addition to having the function of converting O-succinyl-L-homoserine to cystathione (Markus C. Wahl et al., FEBS Letters, Volume 414, Issue 3, 15 September 1997, Pages 492-496, Hiroshi Kanzaki et al., FEMS Microbiology Letters, Volume 33, Issue 1, January 1986, Pages 65-68), L-methionine can be produced using a strain capable of producing a high level of L-threonine. Additionally, the present inventors overexpressed threonine dehydratase, O-succinylhomoserine lyase and cystathionine beta lyase in a non-methionine auxotroph derived from the strain capable of producing a high level of L-threonine. Consequently, it was possible to produce L-methionine at high yield, even in the presence of a high level of methionine without inhibition, as compared with the conventional method using the metA protein.

Further, co-expression of 5,10-methylenetetrahydrofolate reductase and serine hydroxymethytransferase, both involved in donating a methyl group in the methionine biosynthesis pathway, in a strain capable of producing a high level of L-threonine was found to make the strain independent of methionine for growth, and overexpression of glyA and metF genes in the non-methionine auxotroph derived from a strain capable of producing a high level of L-threonine allowed methionine to be produced at high yield.

Furthermore, the application of the L-methionine biosynthesis-involved genes and the methyl group donation-involved genes brought about higher yield in the production of methionine.

DISCLOSURE OF INVENTION

It is an object of the present invention to provide a method of preparing a strain capable of producing L-methionine at high yield, which is transformed with one or more recombinant vectors expressing two or more proteins selected from a group consisting of threonine dehydratase, O-succinylhomoserine lyase, cystathionine beta lyase, 5,10-methylenetetrahydrofolate reductase and serine hydroxymethyltransferase.

It is another object of the present invention to provide the strain prepared by the method.

It is a further object of the present invention to provide a method of producing L-methionine using the strain.

BEST MODE FOR CARRYING OUT THE INVENTION

In accordance with an embodiment, the present invention provides a method of preparing an L-methionine production strain in which an L-threonine production strain is transformed with a recombinant vector(s) capable of expressing two to firve proteins selected from a group consisting of threonine dehydratase, O-succinylhomoserine lyase, cystathionine beta lyase, 5,10-methylenetetrahydrofolate reductase and serine hydroxymethyltransferase.

In a preferred embodiment, the present invention provides a strain capable of producing L-methionine at high yield, transformed from an L-threonine production strain with a recombinant vector capable of overexpressing O-succinylhomoserine lyase, and one or both of cystathionine beta lyase and threonine dehydratase.

In a concrete embodiment, the present invention provides a strain capable of producing L-methionine at high yield by overexpressing a set of threonine dehydratase and O-succinylhomoserine lyase, a set of O-succinylhomoserine lyase and cystathionine beta lyase, or a set of threonine dehydratase, O-succinylhomoserine lyase and cystathionine beta lyase in an L-threonine production strain.

The enzyme threonine dehydratase, as used in the present invention, shows the catalytic activity of hydrolyse threonine to 2-oxobutanoate, as represented by the following reaction formula, and is encoded by tdcB (Datta P, Goss T J, Omnaas J R, Patil R V (1987), Proc Natl Acad Sci USA 1987; 84(2); 393-7), ilvA (Lawther R P, Wek R C, Lopes J M, Pereira R, Taillon B E, Hatfield G W (1987), Nucleic Acids Res 1987; 15(5); 2137-55), and sdaA and B:

L-threonine+H2O<=>2-oxobutanoate+H2O+NH3

O-succinylhomoserine lyase has the activity of synthesis of cystathionine from O-succinyl-L-homoserine and of O-succinyl-L-homoserine from 2-oxobutanoate (2-ketobutyrate, 2-oxobutyric acid, a-oxobutyric acid, α-ketobutyrate, α-ketobutyric acid, 2-oxo-butyrate, 2-keto-butyrate, 2-ketobutyric acid) (Clausen T, Huber R, Prade L, Wahl M C, Messerschmidt A, EMBO J. Dec. 1, 1998; 17(23): 6827-38), as represented by the following formulas, and is encoded by metB (Martel A, Bouthier de la Tour C, Le Goffic F (1987), Biochem Biophys Tes Commun 1987; 147(2); 565-71):

L-cysteine+O-succinyl-L-homoserine<=>succinate+
    cystathionine 2-oxobutanoate+succinate+NH3<=>O-succinyl-L-
    homoserine+H2O Cystathionine beta lyase, as represented by the following formula, functions to metabolize cystathionine, synthesized by O-succinylhomoserine lyase, to homocystein, and is encoded by metC (Dwivedi C M, Ragin R C, Uren J R (1982). Biochemistry 1982; 21(13); 3064-9. PMID: 7049234):

cystathionine+H2O<=>pyruvate+NH3+homocystein

Genes coding for such proteins are cloned in Escherichia coli, and can be obtained from the genomic sequences of E. coli disclosed in literature (Blattner et. al., Science 277: 1453-1462 (1997)) (Accession no. AAC75876). Additionally, the gene sequences are available from databases such as those from the National Center for Biotechnological Informtion (NCBI) and the DNA Data Bank of Japan (DDBJ).

It should be understood that fragments or derivatives of the genes, as long as they can express biologically identical proteins, may be used in the present invention.

The overexpression of each of the respective enzyme proteins may be achieved through a recombinant vector(s) containing each of the genes coding therefor (e.g., tdcB, ilvA, metB, metC). Examples of the recombinant vector can include pSE tdcB-metB, pCL tdcB-metB, pSE ilvA-metB, pCL ilvA-metB, pSE metB-metC, pCL metB-metC, pSE tdcB-metBC, pSE ilvA-metBC, pCL tdcB-metBC, and pCL ilvA-metBC.

The transformation of an L-threonine production strain with the recombinant vectors results in L-methionine production strains.

As used herein, the term "L-threonine production strain" means any prokaryotic or eukaryotic strain that is able to synthesis L-threonine therein. Examples of the L-threonine production strain useful in the present invention can include genera *Escherichia*, *Erwinia*, *Serratia*, *Providencia*, *Corynebacterium* and *Brevibacterium* with the preference for *Escherichia* spp. and further preference for *Escherichia coli*.

Further, mutants as well as wild types can be used as the L-threonine production strains in the present invention. Examples of the mutant strains can include microorganisms of isoleucine-leaky auxotroph, resistance to an L-lysine analog and α-aminobutyric acid; microorganisms in which an endogeneous phosphoenol pyruvate carboxylase (ppc) gene is contained in the genome and additionally, inserted in at least one copy in the chromosomal DNA; microorganisms in which is inactivated the pckA gene that is responsible for the conversion of oxaloacetate (OAA), an intermediate of L-methionine biosynthesis, to phosphoenol pyruvate (PEP); microorganism in which is inactivated the tyrR gene that inhibits the expression of the tyrB gene involved in the biosynthesis of L-methionine; and microorganisms in which is inactivated the galR gene that inhibits the expression of the galP gene involved in sugar transfer. The lysine analog may be selected from among S-(2-aminoethyl)-L-cystein, δ-methyl-L-lysine and combinations thereof. In an embodiment of the present inventon, L-threonine producing and non-L-methionine auxotrophic CJM002, derived from the L-threonine production *Escherichia coli* mutant TF4076 (KFCC 10718, Korean Pat. Publication No. 92-8365), was used. TF4076 shows a methionine requirement, and resistance to methionine analogs (e. g., α-amino-β-hydroxy valeric acid (AHV)), lysine analogs (e. g., S-(2-aminoethyl)-L-cysteine(AEC)), isoleucine analogs (e. g., α-aminobutyric acid), and methionine analogs (e. g., ethionine).

In another preferred embodiment of the present invention, a strain capable of producing L-methionine at high yield is prepared by transforming an L-threonine production strain with a recombinant vector over-expressing serine hydroxymethyltransferase and 5,10-methylenetetrahydrofolate reductase.

When homocysteine is synthesized to methionine by the metH protein, 5,10-methylenetetrahydrofolate reductase and serine hydroxymethyltransferase used in the present invention, as shown in the following formulas, are involved in transferring a methyl group to the homocysteine (Sheppard C A, Trimmer E E, Matthews R G (1999), J Bacteriol 1999; 181(3); 718-25., Shostak K, Schirch V (1988), Biochemistry 1988; 27(21); 8007-14). The gene coding for 5,10-methylenetetrahydrofolate reductase is metF (Saint-Girons I, Duchange N, Zakin M M, Park I, Margarita D, Ferrara P, Cohen G N (1983), Nucleic Acids Res 1983; 11(19); 6723-32) and serine hydroxymethyltransferase is encoded by glyA (Plamann M D, Stauffer L T, Urbanowski M L, Stauffer G V (1983), Nucleic Acids Res 1983; 11(7); 2065-75):

NADH+5,10-methyl-THF<=>NAD+5-methyl-THF

L-serine+THF<=>5,10-methyl-THF+glycine+H$_2$O

Genes coding for the enzymatic proteins are cloned in *Escherichia coli* and can be obtained from the genomic sequences of *E. coli* disclosed in literature (Blattner et. al., Science 277: 1453-1462 (1997)) (Accession no. AAC75876). Additionally, the gene sequences are available from databases such as those from NCBI and DDBJ.

It should be understood that fragments or derivatives of the genes, as long as they can express biologically identical proteins, may be used in the present invention.

In the method, the overexpression of each of the respective enzyme proteins may be achieved through a recombinant vector containing each of the genes coding therefor (e.g., glyA, metF). Preferable examples of the recombinant vector include pSE glyA-metF, pCL glyA-metF.

The transformation of an L-threonine production strain with the recombinant vectors results in L-methionine production strains.

In another preferred embodiment of the present invention, an L-threonine production strain is co-transformed with two or more different recombinant vecors, each expressing two or three proteins selected from among threonine dehydratase, O-succinylhomoserine lyase, cystathionine beta lyase, 5,10-methylenetetrahydrofolate reductase and serine hydroxymethyltransferase to prepare a strain capable of producing L-threonine at high yield.

In a concrete embodiment, an L-threonine production strain is co-transformed with a first recombinant vector expressing O-succinylhomoserine lyase, and one or both of cystathionine beta lyase and threonine dehydratase, and a second recombinant vector expressing 5,10-methylenetetrahydrofolate reductase and serine hydroxymethyltransferase to prepare a strain capable of producing L-threonine at high yield.

In a more concrete embodiment, a strain capable of producing L-methionine at high yield is prepared by transforming an L-threonine production strain with a set of a first recombinant vector expressing threonine dehydratase (tdcB, ilvA) and O-succinylhomoserine lyase and a second recombinant vector expressing serine hydroxymethyltransferase and 5,10-methylenetetrahydrofolate reductase, a set of a first recombinant vector expressing O-succinylhomoserine lyase and cystathionine beta lyase and a second recombinant vector expressing serine hydroxymethyltransferase and 5,10-methylenetetrahydrofolate reductase, or a set of a first recombinant vector expressing threonine dehydratase, O-succinylhomoserine lyase and cystathionine beta lyase and a second recombinant vector expressing serine hydroxymethyltransferase and 5,10-methylenetetrahydrofolate reductase.

In a more preferred embodiment of the present invention, L-methionine is over-expressed in an L-threonine production strain co-transformed with a first recombinant vector expressing threonine dehydratase and O-succinylhomoserine lyase and a second recombinant vector expressing serine hydroxymethyltransferase and 5,10-methylenetetrahydrofolate reductase.

In a most preferred embodiment, an L-threonine production strain is co-transformed with a first recombinant vector expressing threonine dehydratase, O-succinylhomoserine lyase and cystathionine beta lyase and a second recombinant vector expressing serine hydroxymethyltransferase and 5,10-methylenetetrahydrofolate reductase to yield excessive L-methionine.

Of the recombinant vectors containing genes coding for the enzyme proteins (tdcB, ilvA, metB, metC, glyA, metF), the first recombinant vectors are preferably exemplified by pSE tdcB-metB, pCL tdcB-metB, pSE ilvA-metB, pCL ilvA-metB, pSE metB-metC, pCL metB-metC, pSE tdcB-metBC, pSE ilvA-metBC, pCL tdcB-metBC and pCL ilvA-metBC and the second recombinant vectors are preferably exemplified by pSE glyA-metF and pCL glyA-metF.

Preferably, while pSE tdcB-metBC, pSE ilvA-metBC, pCL tdcB-metBC or pCL ilvA-metBC is used as a first recombinant vector, pSE glyA-metF or pCL glyA-metF is used as the second recombinant vector, so as to overexpress all of threonine dehydratase, O-succinylhomoserine lyase, serine hydroxymethyltransferase and 5,10-methylenetetrahydrofolate reductase.

As an L-threonin production strain for use in the method of preparing an L-methionine production strain, non-L-methionine auxotrophic *Escherichia coli* is preferable. More preferable is *Escherichia coli* CJM002, a non-methionine auxotroph, which is mutated from methionine auxotrophic TF4076 using NTG.

In accordance with another embodiment, the present invention provides methods of preparing the L-methionine production strain and of producing L-methionine using the L-methionine production strain.

In a concrete embodiment, the preparation of an L-methionine production strain through gene recombination and the production of L-methionine using the L-methionine production strain are achieved by the following processes:

(1) isolating L-methionine biosynthesis- and/or methyl group donation-involved genes including tdcB, ilvA, metB, metC, metF, and glyA and amplifying them by PCR.

After being isolated from an L-threonine production strain, genomic DNA serves as a template for amplifying genes tdcB, ilvA, metB, metC, metF and glyA. For the amplification of genes tdcB, ilvA, metB, metC, metF and glyA, PCR using oligonucleotide primers targeting the genes may be employed. PCR methods are well known in the art (refer to PCR Protocols: A Guide to Method and Application, Ed. M. Innis et al., Academic Press (1990)). With a genomic DNA, a suitable enzyme, primers and a buffer, PCR may be conducted using a DNA Thermal Cycler (Perkin Elmer Cetus, Norwalk, Conn. USA) for convenience. Positive PCR results are determined by detecting appropriate DNA fragments through, for example, agarose gel electrophoresis.

Genes for use in the overexpression of proteins tdcB, ilvA, metB, metC, metF and glyA in accordance with the present invention include not only polynucleotide sequences containing the genes, but also DNA fragment coding for proteins identical in activity to those encoded by the genes. Further, substitution, deletion and/or insertion mutants are also included within the scope of the present invention as long as they have activity similar to that of the intact.

(2) inserting the genes into an expression vector to construct a recombinant vector.

The genes tdcB, ilvA, metB, metC, metF and glyA are cloned in appropriate T-vectors, followed by introducing the resulting recombinant vectors into host cells such as *E.coli* by transformation. The transformants are cultured and harvested, from which recombinant vectors harboring the genes tdcB, ilvA, metB, metC, metF and glyA are then isolated.

Using restriction enzymes NheI and SacI, the isolated recombinant vectors that contain the corresponding restriction sites, designed upon the synthesis of the primers, are digested, followed by the insertion of the excised DNA fragments into trc promoter-carrying vectors. The resulting tdcB, ilvA, metB, metC, metF and glyA genes are constructed into operon structures such as tdcB-metB, tdcB-metBC, ilvA-metB, ilvA-metBC and glyA-metF.

(3) introducing the recombinant vectors into L-threonine production strain to prepare transformed strains.

The polynucleotide sequences are introduced into strains capable of producing L-threonine and/or L-methionine by a typical technique such as electroporation. Screening by antibiotic resistance allows the selection of strains in which tdcB, ilvA, metB, metC, metF and/or glyA genes are overexpressed.

In the present invention, each of the recombinant plasmids pSE tdcB-metB, pSE tdcB-metBC, pSE ilvA-metB, pSE ilvA-metBC and pSE glyA-metF was introduced by electroporation into non-methionine auxotrophic *Escherichia coli* CJM002, which was mutated from TF4076 having the requirement for isoleucine-leaky and methionine and resistance to L-lysine analogs and a-aminobutyric acid using NTG. The transformed strain was identified to produce a high level of L-methionine compared with the mother strain CJM002.

The L-threonine production strain TF4076 (KFCC 10718, Korean Pat. Publication No. 92-8365) is characterized by methionine requirement and resistance to methionine analogs (e.g., α-amino-β-hydroxy valaric acid, AHV), lysine analogs (e. g., S-(2-aminoethyl)-L-cystein, AEC), isoleucine analogs (e. g., α-aminobutyric acid), and methionine analogs (e. g., ethionine). The entire content of the Korean patent is incorporated herein by reference. Being a methionine auxotroph, TF4076 cannot synthesize methionine therein. In order to serve as a methionine production strain, TF4076 was made to be a non-methionine auxotroph. In this regard, TF4076 was mutated into the threonine production strain *Escherichia coli* CJM002, which does not require methionine for its growth, using NTG.

The threonine production *Escherichia coli* CJM002 which is non-methionine auxotrophic was deposited in the name of *Escherichia coli* MF001 at KCCM (Korean Culture Center of Microorganisms, located in 361-221, Yurim B/D, Hongje-1-dong, Seodaemun-gu, Seoul 120-091, Republic of Korea) on Apr. 9, 2004, with the accession No. KCCM-10568.

The introduction of recombinant vectors carrying tdcB, ilvA, metB, metC, metF and glyA genes or fragments thereof into host cells may be achieved by, for example, transformation, conjugation, transduction or electroporation, but is not limited thereto.

(4) culturing the transformed strains to produce L-methionine.

The cultivation of the prepared L-methionine overexpression microorganisms may be conducted using appropriate media and culture conditions well known in the art. According to strains used, culturing procedures can be readily adjusted by those skilled in the art. Examples of the culturing procedures include batch type, continuous type and fed-batch type manners, but are not limited thereto. Various culturing procedures are disclosed in literature ("Biochemical Engineering" by James M. Lee, Prentice-Hall International Editions, pp 138-176).

Culturing Media must properly satisfy the demands of the strains to be cultured. Media for a variety of microorganism are disclosed in the literature ("Manual of Methods for General Bacteriology" by the American Society for Bacteriology, Washington D.C., U.S.A., 1981). Typically culture media contain various carbon sources, nitrogen sources and minerals. Examples of the carbon sources useful in the present invention include carbohydrates, such as glucose, sucrose, lactose, fructose, maltose, starch, cellulose, etc.; lipids, such as soybean oil, sunflower seed oil, castor oil, and coconut oil; fatty acids, such as palmitic acid, stearic acid, linoleic acid, etc., alcohol, such as glycerol and ethanol, and organic acids, such as acetic acid. These carbon sources may be used alone or in combination. Examples of nitrogen sources useful in the present invention include organic nitrogen sources such as peptone, yeast extract, broth, malt extract, corn steep liquor and soy bean, and inorganic nitrogen sources such as urea, ammonium sulfate, ammonium chloride, ammonium phosphate, ammonium carbonate and ammonium nitrate. These nitrogen sources may be used alone or in combination. To the media, phosphorus sources, such as potassium dihydrogen phosphate, dipotassium hydrogen phosphate or corresponding sodium-containing salts, may be added. In addition, the media may contain metal salts such as magnesium sulfate or ferrous sulfate. Further, the media may be supplemented with amino acids, vitamins, and appropriate precursors. These media or precursors may be added to cultures by a batch type or continuous type method.

During cultivation, ammonium hydroxide, potassium hydroxide, ammonia, phosphoric acid, and/or sulfuric acid may be properly added so as to adjust the pH of the cultures. Defoaming agents, such as ammonium hydroxide, potassium hydroxide, phosphoric acid and sulfuric acid may be properly added so as to reduce the formation of foams in cultures. To maintain the cultures in aerobic states, oxygen or oxygen-containing gas (e.g., air) may be injected into the cultures. The cultures are maintained at 20° C. to 45° C. and preferably at 25° C. to 40° C. Culturing may be continued until a desired amount of L-methionine is obtained, and is preferably conducted for 0 to 160 hours.

In order to overexpress threonine dehydratase, O-succinyl-homoserine lyase, cystathionine beta lyase, 5,10-methylene-tetrahydrofolate reductase, and serine hydroxymethyltransferase in a microorganism capable of production of a high level of L-threonine, promoters for controlling the expression of genes coding for the proteins are changed with overexpression promoters such as trc, tac, etc., and/or the expression control of transcription factors, such as metJ inactivation, metR overexpression, tdcR, tdcA overexpression, etc., is conducted.

The methionine produced in accordance with the present invention is of L configuration. All Amino acids synthesized in vivo occur in the L-configuration and, being readily utilized in organisms, amino acids in the L-configuration have an advantage over those in the D-configuration. L-methionine finds applications in various industries, such as an additive for foods and foodstuff, a medicinal material, a sulfur source, a medicine, etc.

In one important metabolism pathway, L-methionine is adenylated to form S-adenosyl-methionine. Thus, as the biosynthesis of L-methionine actively occurs, the amount of its important metabolite S-adenosyl-methionine also increases.

Therefore, in accordance with another aspect of the present invention, the present invention provides the production of S-adenosyl-methionine and more particularly, a method of preparing an S-adenosyl-methionine production strain, a strain prepared by the method, and a method of producing S-adenosyl-methionine using the strain.

A better understanding of the present invention may be obtained through the following examples which are set forth to illustrate, but are not to be construed as the limit of the present invention.

EXAMPLE 1

Figure 1:
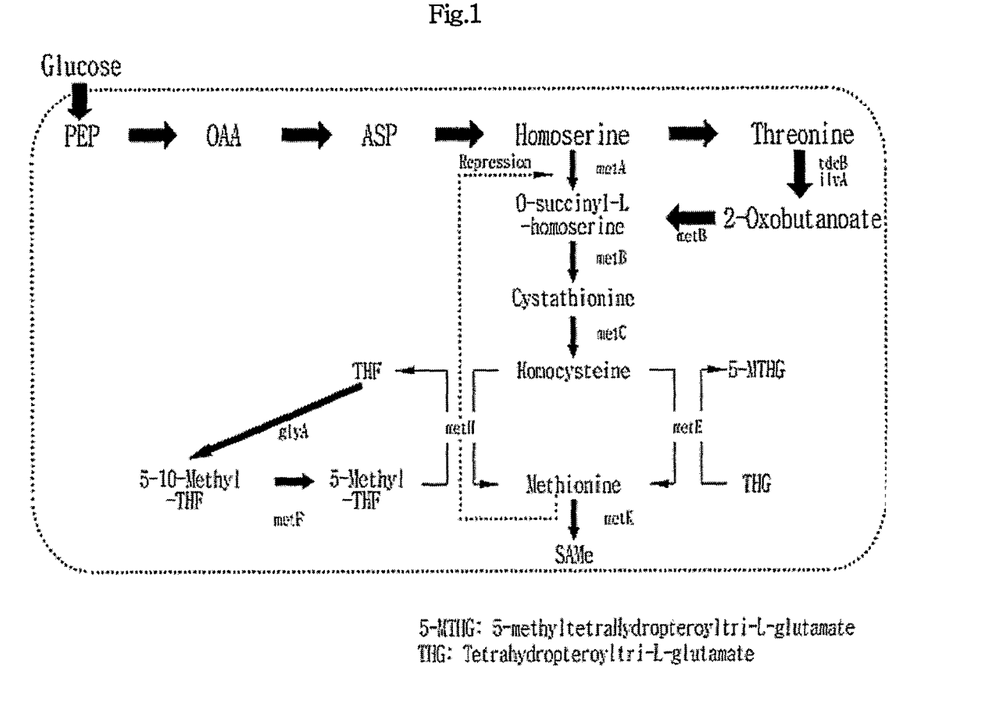
FIG. 1 is a view illustrating the methionine biosynthesis pathway occurring in the strain prepared according to the present invention.
Figure 2:
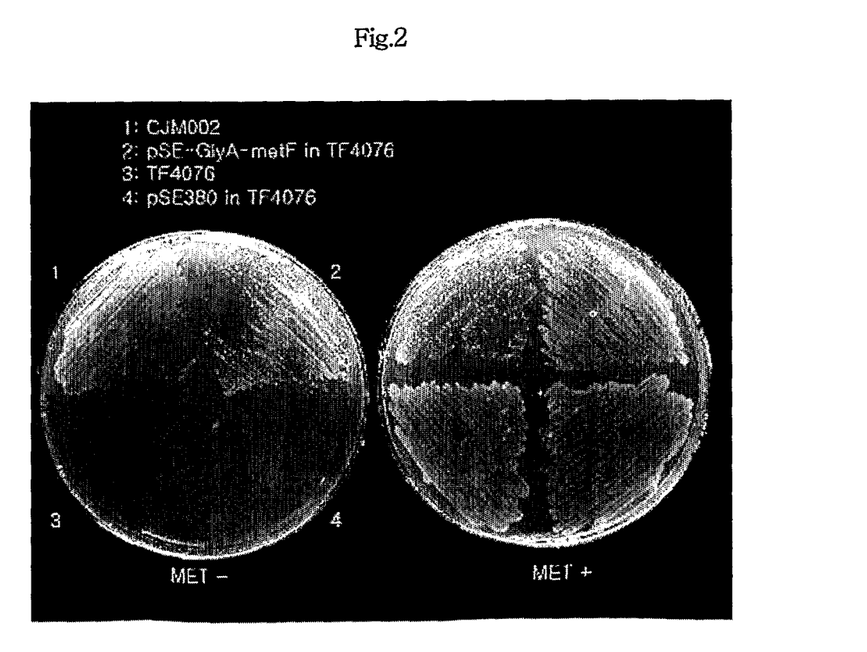
FIG. 2 is a photograph showing culture results obtained after the CJM002 strain, which has been freed from the methionine requirement by mutation, and the non-methionine auxotrophic strain, which has been transformed from the methionine auxotrophic TF4076 with glyA-metF, have been cultured on two agar plates, respectively, supplemented with and free of methionine.

Removal of TF4076 Strain from Methionine Requirement 1-1) Removal from Methionine Requirement by Mutation The mutant strain TF4076 (KFCC10718, Korean Pat. Publication No. 92-8365) is a methionine auxotroph. To remove the methionine requirement, TF4076 was subjected to a mutation experiment using NTG (1-Methyl-3-Nitro-1-Nitrosoguanidine). TF4076 was cultured overnight in an LB broth and then, for 6 hours in a fresh LB broth. The cell mass obtained by the centrifugation of the culture was resuspended twice in saline solution and the suspension was centrifuged to obtain a cell pellet. After being resuspended in a citrate buffer, the cells were cultured for 30 min in the presence of 400 ug/ml of NTG. After the mutation treatment, the cells were separated by centrifugation, resuspended twice in saline solution, and cultured in an M9 minimal agar ($Na_2HPO_4$ 12.8 g/L, $KH_2PO_4$ 3 g/L, NaCl 0.5 g/L, NH4Cl 1 g/L, 20% Glucose 10 ml/L, 1M $CaCl_2$ 0.1 ml/L, 1M $MgSO_4$ 2 ml/L) to select non-methionine auxotrophic cells which were grown thereon. FIG. 2 shows cells which have been freed from the methionine requirement. The non-methionine auxotrophic threonine production strain was named CJM002.

The non-methionine auxotrophic threonine production strain *Escherichia coli* CJM002 was deposited in the name of *Escherichia coli* MF001 at the KCCM on Apr. 9, 2004, with the accession No. KCCM-10568.

1-2) Removal from Methionine Requirement by Gene Substitution

The mutant strain TF4076 is a methionine auxotroph. To be released from the methionine requirement, TF4076 was compared with its wild type with regard to the DNA sequences of genes responsible for methionine biosynthesis. Of them, glyA and metF genes of TF4076, which were found to have significant differences from the corresponding genes of the wild type, were substituted with the wild type's. As a result, the TF4076 strain carrying the wild type's glyA and metF genes was identified not to require methionine for its growth. The construction of the plasmid pSE glyA-metF which was used to remove the methionine requirement was described in detail in Example 3, below. FIG. 2 shows cells which have been freed from the methionine requirement.

EXAMPLE 2

Construction of Recombinant Plasmids Carrying tdcB, ilvA, metB, metC, metF, and glyA In this example, a trc promoter was added to each of the genes tdcB, ilvA, metB, metC, metF and glyA which code for threonine dehydratase, O-succinylhomoserine lyase, cystathionine beta lyase, 5,10-methylenetetrahydrofolate reductase, and serine hydroxymethytransferase of *Escherichia coli*, and vectors carrying them were constructed.

First, genomic DNA was isolated from the threonine production *E.coli* strain TF4076 (KFCC 10718) with the aid of the Genomic-tip system (QIAGEN). While the genomic DNA preparation served as a template, polymerase chain reacton (PCR) was performed in the presence of the primers of Table 1, below, with 30 cycles of denaturating at 94° C. for 30 sec, annealing at 60° C. for 30 sec, and extending at 72° C. for 1 min to 3.5 min, to obtain ORF(Open Reading Frame) DNA fragments of tdcB, ilvA, metB, metC, metF and glyA genes, which are about 1003 bp, 1558 bp, 1161 bp, 1185 bp, 903 bp, and 1266 bp long, respectively.

TABLE 1

Primer Sequence Nos. of Genes

| Genes | Primer SEQ. Nos. |
|---|---|
| tdcB | 1, 2 |
| ilvA | 3, 4 |
| metB | 5, 6 |
| metC | 7, 8 |
| glyA | 9, 10 |
| metF | 11, 12 |
| Trc-Sac I | 13 |
| Trc-Xho I | 14 |

The PCR products thus obtained were electrophoresed on 1.0% agarose gel and DNAs were purified from the bands read at sizes of 1003 bp, 1558 bp, 1161 bp, 1185 bp, 903 bp, and 1266 bp. The DNA fragments purified were ligated into pCR2.0 cloning vectors (Invitrogen Co.) at 16° C. overnight. The recombinant plasmids thus obtained, that is, pTotdcB, pToilvA, pTometB, pTometC, pToglyA and pTometF were transformed into E.coli NM522 which was then smeared on agar plates containing carbenicillin (50 mg/L) and cultured at 37° C. overnight.

Using a platinum loop, the colonies were inoculated in 3 ml of LB broth which was then incubated overnight, followed by separating plasmid DNAs with the aid of QIAGEN mini prep kit (QIAGEN). The treatment of the plasmid DNAs with the restriction enzymes NheI and SacI produced fragments carrying ORFs of respective genes. These fragments were ligated at 16° C. overnight to the trc promoter-carrying vector pSE380 (Invitrogen Co.) which was already digested with NheI and SacI. The recombinant plasmids thus obtained, that is, pSE tdcB, pSE ilvA, pSE metB, pSE metC, pSE glyA, and pSE metF were introduced into E. coli NM522 which was then smeared on agar plates containing carbenicillin (50 mg/L) and cultured at 37° C. overnight.

Figure 3:
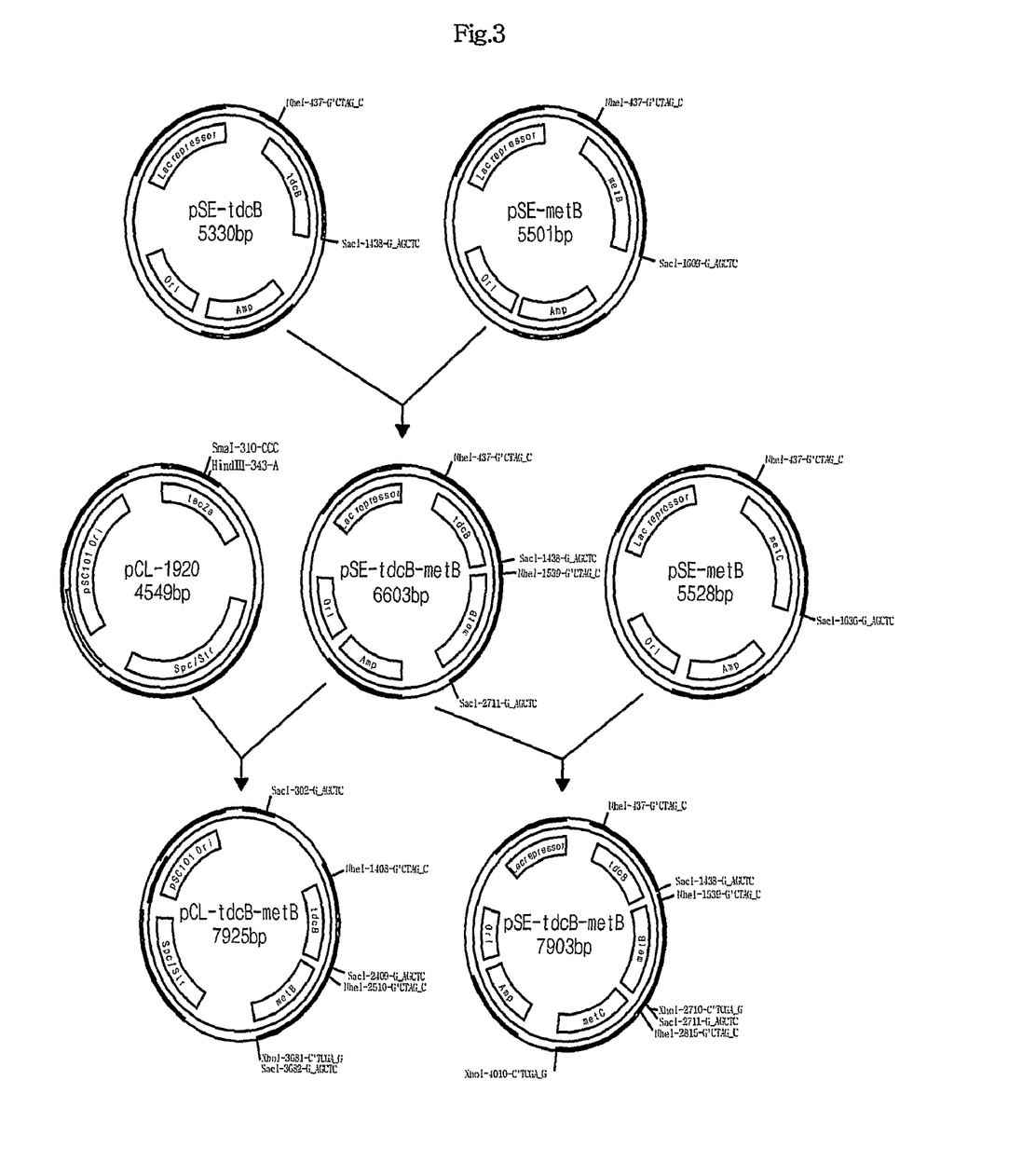
FIG. 3 is a scheme of constructing plasmids pSE tdcB-metB, pSE tdcB-metBC, and pCL tdcB-metB carrying tdcB-metB and tdcB-metBC operon structures which are construced from tdcB, metB, and metC genes, with the plasmids pSEtdcB, pSEmetB and pSEmetC serving as templates for operon construction.

After being transformed with the recombinant plasmids pSE tdcB, pSE ilvA, pSE metB, pSE metC, pSE metF, and pSE glyA, E. coli NM522 was smeared on LB agar plates containing both carbenicillin and ganamycin (50 mg/L, each) and cultured at 32° C. overnight. Using a platinum loop, the colonies formed were inoculated in 3 mL of carbenicillin-containing broth which was then cultured overnight. Subsequently, plasma DNAs were isolated using a QIAGEN mini prep kit (QIAGEN). FIG. 3 shows gene maps of the recombinant plasmids pSE tdcB, pSE ilvA, pSE metB, pSE metC, pSE metF, and pSE glyA.

EXAMPLE 3

Construction of Plasmids Carrying tdcB-metB, tdcB-metBC, ilvA-metB, ilvA-metBC, and glyA-metF Operon Structures In this Example, in order to simultaneously overexpress threonine dehydratase, O-succinylhomoserine lyase, cystathionine beta lyase, serine hydroxymethyltransferase, and 5,10-methylenetetrahydrofolate reductase in E. coli, a set of the tdcB gene and the metB gene, a set of the tdcB gene and the metBC gene, a set of the ilvA gene and the metB gene, a set of the ilvA gene and the metBC gene, and a set of the glyA gene and the metF gene were constructed in operon structures which were then developed into vectors. These vectors were introduced into E. coli host cells, and plasmids were constructed which can overexpress a set of threonine dehydratase and O-succinylhomoserine lyase, a set of threonine dehydratase, O-succinylhomoserine lyase and cystathionine beta lyase, or a set of 5,10-methylenetetrahydrofolate reductase and serine hydroxymethytransferase.

In order to construct operon structures containing tdcB-metB, ilvA-metB, and glyA-metF in addition to a trc promoter from the plasmids constructed in Example 2, the plasmids pSE metB and pSE metF which carry metB metF gene respectively, were used as templates for PCR which was conducted in the presence of primer sets of SEQ. NOS. 13 and 6, and SEQ. NOS. 13 and 12, with 30 cycles of denaturating at 94° C. for 30 sec, annealing at 60° C. for 30 sec, and extending at 72° C. for 1 min to 1.5 min. As a result, ORF DNA fragments containing metB and metF in addition to the ribosomal binding site of the trc promoter were obtained at sizes of about 1279 bp and 903 bp, respectively.

In this regard, the PCR products thus obtained were electrophoresed on 1.0% agarose gel and DNA fragments were purified from the bands read at sizes of 1279 bp and 903 bp. The purified DNAs were ligated to a pCR2.0 cloning vector (Invitrogen Co.) at 16° C. overnight. The recombinant plasmids thus obtained, that is, pTRmetB and pTRmetF, were transformed into E.coli NM522, which was then smeared on agar plates containing carbenicillin (50 mg/L) and cultured at 37° C. overnight.

Using a platinum loop, the colonies were inoculated in 3 ml of LB broth which was then incubated overnight, followed by separating plasmid DNAs with the aid of a QIAGEN mini prep kit (QIAGEN). The treatment of the plasmid DNAs with the restriction enzyme SacI produced fragments carrying metB, the RBS of the metF gene, and an ORF. These fragments were ligated at 16° C. overnight to the trc promoter-carrying vectors pSE tdcB, pSE ilvA, and pSE glyA, which were aready treated with SacI. The recombinant plasmids thus obtained, that is, pSE tdcB-metB, pSE ilvA-metB, and pSE glyA-metF were introduced into E. coli NM522 which was then smeared on agar plates containing carbenicillin (50 mg/L) and cultured at 37° C. overnight.

Using a platinum loop, the colonies formed were inoculated into 3 mL of broth containing carbenicillin and ganamycin, and then cultured overnight. Plasmid DNAs were isolated using a QIAGEN mini prep kit (QIAGEN).

In order to construct operon structures containing tdcB-metBC and ilvA-metBC in addition to a trc promoter, from the plasmids constructed in Example 2, the plasmid pSE metC which carries the metC gene, was used as a template for a PCR which was conducted in the presence of a primer set of SEQ. NOS. 14 and 8, with 30 cycles of denaturating at 94° C. for 30 sec, annealing at 60° C. for 30 sec, and extending at 72° C. for 1 min to 1.5 min. As a result, an ORF DNA fragment containing metC in addition to the ribosomal binding site of the trc promoter was obtained at a size of about 1306 bp.

In this regard, the PCR product thus obtained was electrophoresed on 1.0% agarose gel and a DNA fragment was purified from the bands read at a size of 1306 bp. The purified DNA was ligated to pCR2.0 cloning vector (Invitrogen Co.) at 16° C. overnight. The recombinant plasmid thus obtained, that is, pTRmetC, was transformed into E.coli NM522 which was then smeared on agar plates containing carbenicillin (50 mg/L) and cultured at 37° C. overnight.

Using a platinum loop, the colonies were inoculated in 3 ml of LB broth which was then incubated overnight, followed by separating a plasmid DNA with the aid of a QIAGEN mini prep kit (QIAGEN). The treatment of the plasmid DNA with the restriction enzyme XhoI produced a fragment carrying the RBS of the metC gene, and an ORF. This fragment was ligated at 16° C. overnight to each of the trc promoter-carrying vectors pSE tdcB-metB and pSE ilvA-metB, which were aready treated with XhoI. The recombinant plasmids thus obtained, that is, pSE tdcB-metBC and pSE ilvA-metBC, were introduced into *E. coli* NM522 which was then smeared on agar plates containing carbenicillin (50 mg/L) and cultured at 37° C. overnight.

Using a platinum loop, the colonies formed were inoculated into 3 mL of broth containing carbenicillin and ganamycin, and then cultured overnight. Plasmid DNAs were isolated using a QIAGEN mini prep kit (QIAGEN).

Figure 4A:
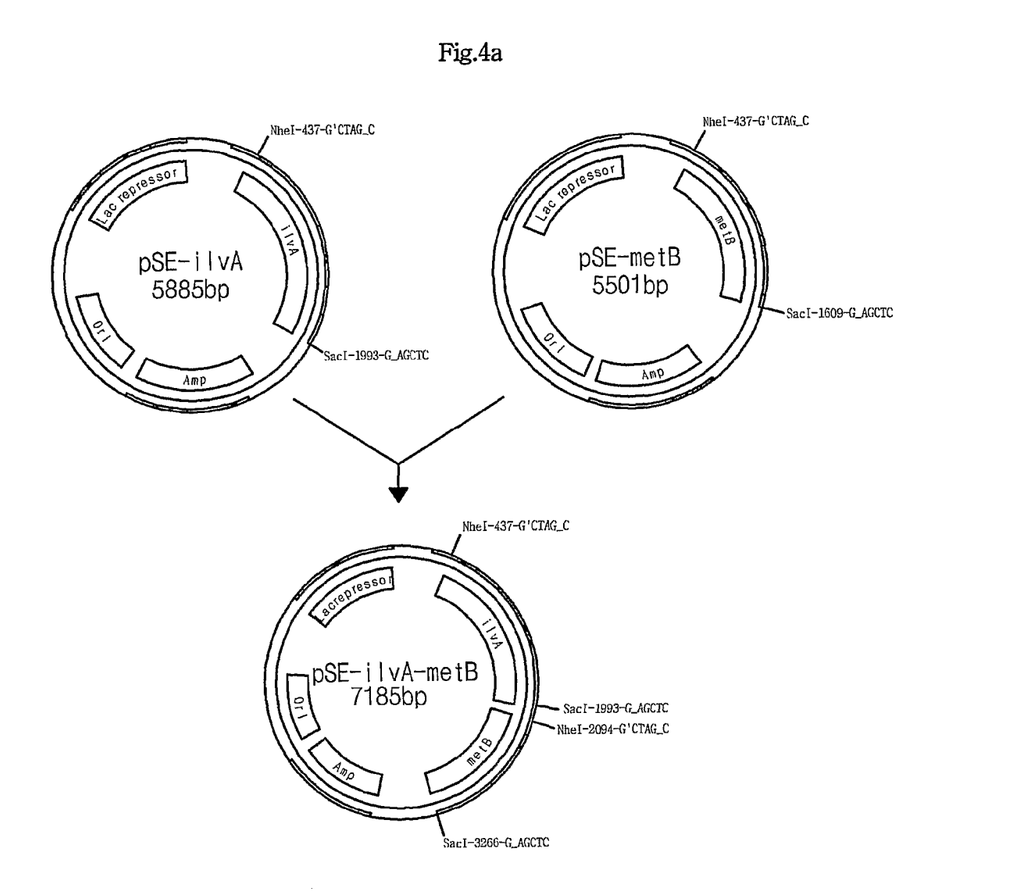
FIG. 4 is schemes of constructing plasmids pSE ilvA-metB and pSE ilvA-metBC carrying operon structures of ilvA, metB and metC genes, with the plasmid pSEilvA serving as a template for operon construction.
Figure 4B:
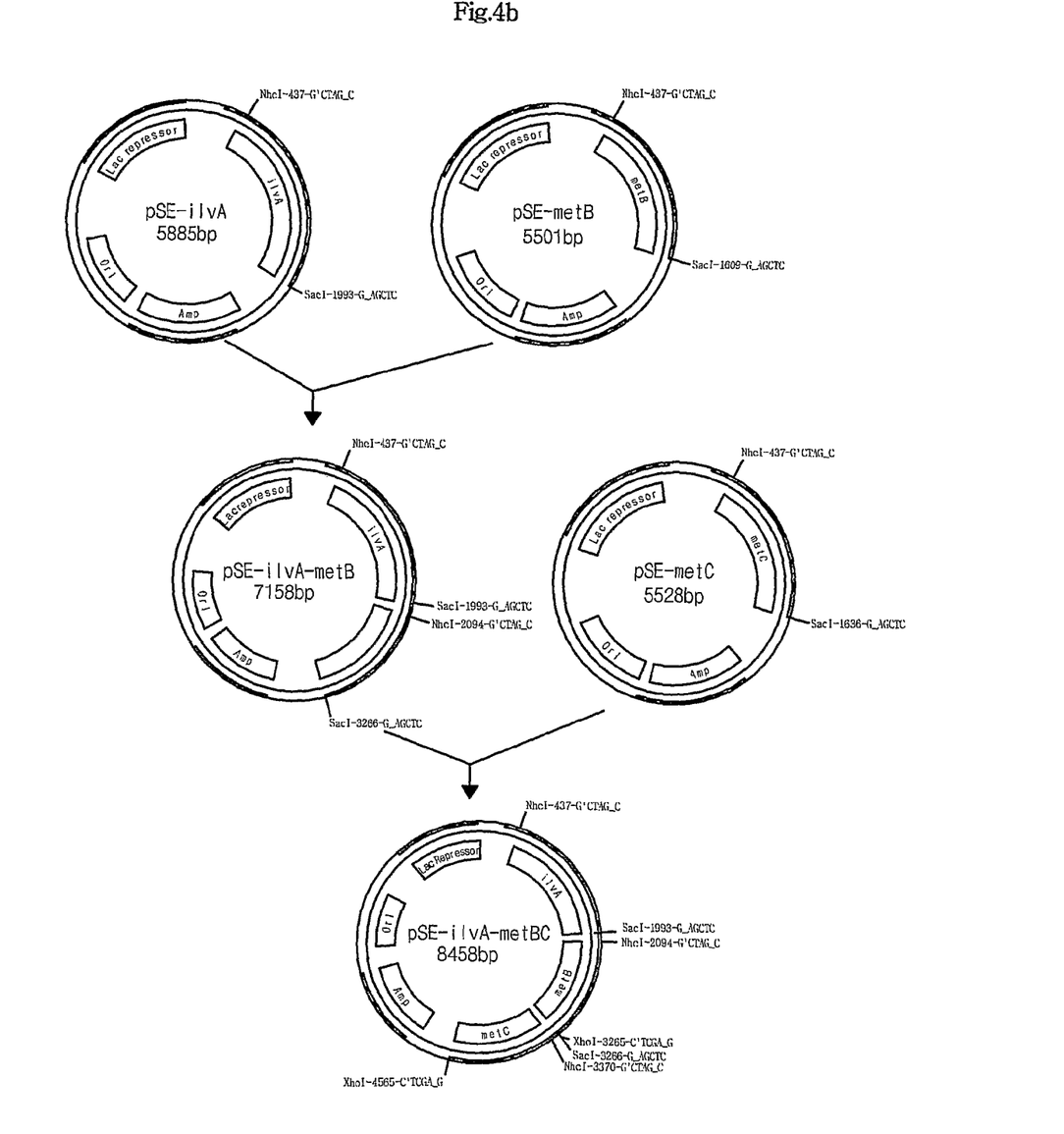
Figure 5:
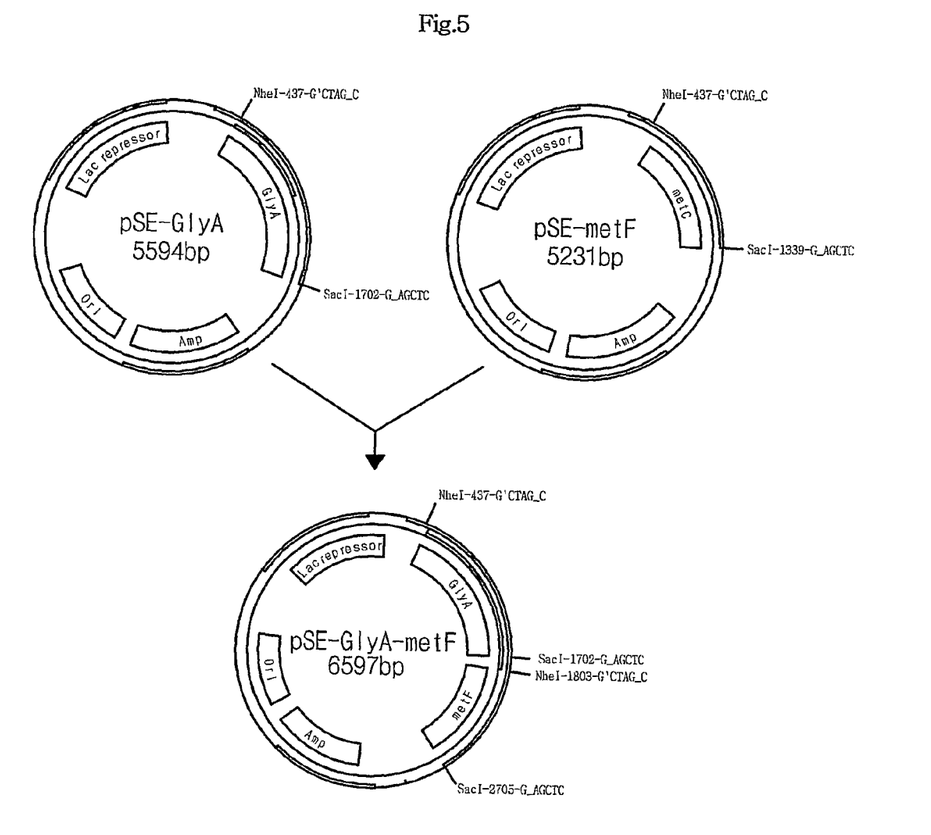
FIG. 5 is a scheme of constructing the plasmid pSE glyA-metF carrying a glyA-metF operon structure which is con-structed from glyA and metF genes, with the plasmids pSEg-lyA and pSEmetF serving as templates for operon construction.

FIGS. 3 to 5 show gene maps of the constructed recombinant plasmids pSE tdcB-metB, pSE ilvA-metB, pSE ilvA-metBC, pSE tdcB-metBC, and pSE glyA-metF.

The recombinant plasmids pSE tdcB-metBC, pSE ilvA-metBC and pSE glyA-metF were introduced into *Escherichia coli* CJM004(pSE tdcB-metBC), *Escherichia coli* CJM005 (pSE ilvA-metBC) and *Escherichia coli* CJM006(pSE glyA-metF) and deposited at the KCCM (Korean Culture Center of Microorganisms, located in 361-221, Yurim B/D, Hongje-1-dong, Seodaemun-gu, Seoul 120-091, Republic of Korea) on Jun. 14, 2004, with the accession Nos. KCCM-10577, KCCM-10578 and KCCM-10579, respectively.

EXAMPLE 4

Construction of Recombinant Plasmid Carrying pSC101 Ori and tdcB-metB Operon

In order to simultaneously express both the constructed tdcB-metB operon and the glyA-metF operon responsible for the methyl recycling in the methionine biosynthesis pathway in a production strain with the aid of two plasmids, a tdcB-metB operon was cloned in the vector pCL1920 which has a recombinant origin different from that of the plasmid pSE380.

After treatment of the plasmid pSE tdcB-metB constructed in Example 3 with restriction enzymes Pvu II and Hind III and the vector pCL1920 carrying a spectinomycin-resistant gene and a pSC101 Ori with restriction enzymes Sma I and Hind III, the digests were electrophoresed on 1.0% agarose gel, followed by DNA purification from bands read at sizes of about 3.4 kb and 4.5 kb. The purified DNA fragments were ligated at 16° C. to a plasmid overnight. The recombinant plasmid pCL tdcB-metB thus obtained was transformed into *E. coli* NM522 which was then smeared on an agar plate containing carbenicillin (50 mg/L) and spectinomycin (100 mg/L) and incubated at 37° C. overnight.

Using a platinum loop, the colonies formed were inoculated into 3 mL of broth containing carbenicillin and spectinomycin, and then cultured overnight. A plasmid DNA was isolated using a QIAGEN mini prep kit (QIAGEN).

FIG. 3 shows gene maps of the constructed recombinant plasmid pCL tdcB-metB.

EXAMPLE 5

Preparation of Methionine Production Strains Harboring the Recombinant Plasmids pSE tdcB-metB, pSE tdcB-metBC, pSE ilvA-metB, pSE ilvA-metBC, and pSE glyA-metF By electroporation, the threonine production strain CJM002, which is a non-methionine auxotroph, was transformed with the recombinant plasmids pSE tdcB-metB, pSE tdcB-metBC, pSE ilvA-metB, pSE ilvA-metBC, and pSE glyA-metF constructed in Example 3, and the transformed cells were smeared on agar plates containing carbenicillin (50 mg/L) and incubated at 37° C. overnight to form colonies.

EXAMPLE 6

Preparation of Methionine Production Strain Carrying both the Recombinant Plasmids pSE glyA-metF and pCL tdcB-metB Using electroporation, the recombinant plasmids pSE glyA-metF and pCL tdcB-metB, which were constructed in Examples 3 and 4, respectively, were introduced into the threonine production strain CJM002, which does not require methionine for its growth, and the transformed cells were smeared on agar plates containing both carbenicillin (50 mg/L) and spectinomycin (100 mg/L) and incubated at 37° C. overnight to form colonies.

EXAMPLE 7

Test of Prepared Strains for Methionine Production Titer in Erlenmeyer Flask 30 coloinies were selected from each of the strains that had been grown on agar plates in the presence of carbenicillin and in the co-existence of carbenicillin and spectinomycin as in Examples 5 and 6 and were compared for methionine production in Erlenmeyer flasks using the methionine titer medium shown in Table 2, below.

TABLE 2

| Methionine Titer Medium | |
|---|---|
| Composition | Conc. (per liter) |
| Glucose | 40 g |
| Ammonium sulfate | 28 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium Carbonate | 30 g |
| Vitamin B12 | 0.02 mg |
| IPTG | 0.1 mM |
| $CaCO_3$ | 30 g |
| Yeast Extract | 2 g | pH (7.0)

Single colonies which were cultured on LB agar plates at 31° C. overnight in an incubator were inoculated by one platinum loop into 25 ml of the titer medium and incubated at 31° C. for 48 hours, with shaking at 200 rpm.

L-methionine from the cultures was analyzed by HPLC. The analysis results are given in Table 3, below. Whereas the mother strain *E. coli* CJM002 produced 5 mg/L or less of L-methionine during 48 hours fermentation, as is apparent from the data of Table 2, the mutant strains harboring pSE tdcB-metB, pSE tdcB-metBC, pSE ilvA-metB, and pSE glyA-metF showed L-methionine production capacities of 40, 66, 48, 50, and 47.7 mg/L, respectivlty for 48 hours, with a peak of 160 mg/L obtained for L-methionine productivity in the strain harboring both pCL tdcB-metB and pSE glyA-metF plasmids.

TABLE 3

Results of Flask Titer Test of Recombinant Strains

| Strains | CJM002 | CJM002 | CJM002 | CJM002 | CJM002 | CJM002 | CJM002 |
|---|---|---|---|---|---|---|---|
| Plasmid 1 (ColE1 Ori) |  | pSE tdcB-metB | pSE tdcB-metBC | pSE ilvA-metB | pSE ilvA-metBC | pSE glyA-metF | pSE glyA-metF |
| Plasmid 2 (Psc101 Ori) |  |  |  |  |  |  | pCL tdcB-metB |
| L-threonine (g/L) | 16.0 | 7.5 | 5.9 | 6.0 | 6.1 | 11.5 | 5.6 |
| L-methionine (mg/L) | 5 | 40 | 66 | 48 | 50 | 47.7 | 160 |

Taken together, the data obtained in the above Examples demonstrate that the threonine production strains can be improved in methionine biosynthesis capacity through the overexpression of threonine dehydratase, O-succinylhomoserine lyase, and cystathionine beta lyase protein therein. This is, in the present inventors' opinion, attributed to the fact that 2-oxobutanoate, a lysate resulting from the catalytic action of threonine dehydratase, is utilized for methionine biosynthesis by O-succinylhomoserine lyase and cystathionine beta lyase. In addition, when 5,10-methylenetetrahydrofolate reductase and serine hydroxymethytransferase, both responsible for methyl recycling in the methionine biosynthesis pathway, are excessively expressed, the methionine production capability is also improved. Particularly, the co-expression of a set of a first plasmid expressing threonine dehydratase and O-succinylhomoserine lyase (or threonine dehydratase, O-succinylhomoserine lyase and cystathionine beta lyase) and a second plasmid expressing 5,10-methylenetetrahydrofolate reductase and serine hydroxymethytransferase brings about a great improvement in L-methionine biosynthesis capability.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

L-methionine, applicable to a variety of industries including the food industry, the medicine industry, etc., can be effectively produced at low cost using the L-methionine production strains prepared according to the present invention.

The invention claimed is:

1. An L-methionine production bacterial strain, wherein the strain has the ability to produce L-threonine, and is transformed with one or more recombinant vectors expressing (a) threonine dehydratase; and (b) at least one of the proteins selected from a group consisting of O-succinylhomoserine lyase, cystathionine beta lyase, 5,10-methylenetetrahydrofolate reductase and serine hydroxymethyltransferase.

2. The L-methionine production strain as set forth in claim 1, wherein the strain is transformed with a recombinant vector expressing threonine dehydratase, O-succinylhomoserine lyase and cystathionine beta lyase.

3. A method of producing L-methionine, in which the L-methionine production strain of claim 1 is fermented.

4. The L-methionine production strain as set forth in claim 1, wherein the strain is transformed with a recombinant vector expressing threonine dehydratase, 5,10-methylenetetrahydrofolate reductase and serine hydroxymethyltransferase.

5. The L-methionine production strain as set forth in claim 1, wherein the strain is transformed with a recombinant vector expressing threonine dehydratase, O-succinylhomoserine lyase, cystathionine beta lyase. 5,10-methylenetetrahydrofolate reductase and serine hydroxymethyltransferase.

6. The L-methionine production strain as set forth in claim 1, wherein the strain does not require methionine for growth.

7. The L-methionine production strain as set forth in claim 2, wherein the strain does not require methionine for growth.

8. The L-methionine production strain as set forth in claim 4, wherein the strain does not require methionine for growth.

9. The L-methionine production strain as set forth in claim 5, wherein the strain does not require methionine for growth.

10. The L-methionine production strain as set forth in claim 1, wherein the strain is prepared by transforming *Escherichia coli* MF001(KCCM-10568) with one or more recombinant vectors expressing (a) threonine dehydratase; and (b) at least one of the proteins selected from a group consisting of O-succinylhomoserine lyase, cystathionine beta lyase, 5,10-methylenetetrahydrofolate reductase and serine hydroxymethyltransferase.

11. A method of producing L-methionine, in which the L-methionine production strain of claim 2 is fermented.

12. A method of producing L-methionine, in which the L-methionine production strain of claim 4 is fermented.

13. A method of producing L-methionine, in which the L-methionine production strain of claim 5 is fermented.

14. A method of producing L-methionine, in which the L-methionine production strain of claim 6 is fermented.

15. A method of producing L-methionine, in which the L-methionine production strain of claim 7 is fermented.

* * * * *

SEQUENCE LISTING

```
<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
gctagcaatg catattacat acgatctgcc                                     30

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
gagctcttaa gcgtcaacga aaccgg                                         26

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
```

```
gctagcaatg gctgactcgc aaccc                                          25

<210> SEQ ID NO 4
<211> LENGTH: 26
<212> TYPE: DNA
<213> ORGANISM: Artificial Sequence
<220> FEATURE:
<223> OTHER INFORMATION: Synthetic

<400> SEQUENCE: 4
gagctcctaa cccgccaaaa agaacc                                         26

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
gctagccatg acgcgtaaac aggc                                           24

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
gagctcttac cccttgtttg cagccc                                         26

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
gctagccatg gcggacaaaa agct                                           24

<210> SEQ ID NO 8
<211> LENGTH: 26
<212> TYPE: DNA
<213> ORGANISM: Artificial Sequence
<220> FEATURE:
<223> OTHER INFORMATION: Synthetic

<400> SEQUENCE: 8
gagctcttat acaattcgcg caaaac                                         26

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
gctagcgatg ttaaagcgtg aaat                                           24

<210> SEQ ID NO 10
<211> LENGTH: 26
<212> TYPE: DNA
```

```
<213> ORGANISM: Artificial Sequence
<220> FEATURE:
<223> OTHER INFORMATION: Synthetic

<400> SEQUENCE: 10
gagctcttat gcgtaaaccg ggtaac                                           26

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
gctagctatg agctttttc acgc                                              24

<210> SEQ ID NO 12
<211> LENGTH: 26
<212> TYPE: DNA
<213> ORGANISM: Artificial Sequence
<220> FEATURE:
<223> OTHER INFORMATION: Synthetic

<400> SEQUENCE: 12
gagctcttat aaaccaggtc gaaccc                                           26

<210> SEQ ID NO 13
<211> LENGTH: 26
<212> TYPE: DNA
<213> ORGANISM: Artificial Sequence
<220> FEATURE:
<223> OTHER INFORMATION: Synthetic

<400> SEQUENCE: 13
gagctcgagg taattataac ccgggc                                           26

<210> SEQ ID NO 14
<211> LENGTH: 26
<212> TYPE: DNA
<213> ORGANISM: Artificial Sequence
<220> FEATURE:
<223> OTHER INFORMATION: Synthetic

<400> SEQUENCE: 14
ctcgaggagg taattataac ccgggc                                           26
```